United States Patent [19]
Bergquist et al.

[11] Patent Number: 5,817,079
[45] Date of Patent: Oct. 6, 1998

[54] SELECTIVE PLACEMENT OF ABSORBENT PRODUCT MATERIALS IN SANITARY NAPKINS AND THE LIKE

[75] Inventors: Roger Bergquist, Ringoes; Peter Jackson, Hampton; Subramanian Srinivasan, East Brunswick; Martin Wislinski, Edison; Edmund DeRossett, Mercerville; James A. Bradstreet, Colts Neck; Philip Stevenson, Princeton; Schmuel Dabi, Highland Park, all of N.J.

[73] Assignee: McNeil-PPC, Inc., Skillman, N.J.

[21] Appl. No.: 195,894

[22] Filed: Feb. 10, 1994

Related U.S. Application Data

[63] Continuation of Ser. No. 970,532, Nov. 2, 1992, abandoned, which is a continuation of Ser. No. 879,081, May 1, 1992, abandoned, which is a continuation of Ser. No. 717,166, Jun. 17, 1991, abandoned, which is a continuation of Ser. No. 498,017, Mar. 27, 1990, abandoned, which is a continuation-in-part of Ser. No. 334,960, Apr. 14, 1989, abandoned.

[30] Foreign Application Priority Data

Apr. 4, 1989 [GB] United Kingdom .................... 8911772

[51] Int. Cl.[6] ...................................................... A61F 13/15
[52] U.S. Cl. .................. 604/378; 428/299.1; 428/301.4; 428/484; 604/365; 604/370
[58] Field of Search ............................ 604/358, 365–368, 604/370, 372, 378–381, 385.1; 428/299, 301, 481, 299.1

[56] References Cited

U.S. PATENT DOCUMENTS

| | | | |
|---|---|---|---|
| 2,331,355 | 10/1943 | Strongson | 604/385.1 |
| 3,183,908 | 5/1965 | Roehr | 128/290 |
| 3,582,462 | 6/1971 | Ashikaga et al. . | |
| 3,589,978 | 6/1971 | Kamal et al. . | |
| 3,683,917 | 8/1972 | Comerford | 604/381 |
| 3,771,525 | 11/1973 | Chapuis . | |
| 3,913,578 | 10/1975 | Schaar | 604/378 |
| 3,996,936 | 12/1976 | Widkund et al. . | |
| 4,015,604 | 4/1977 | Csillag | 128/287 |
| 4,026,291 | 5/1977 | Nagano et al. | 604/368 |
| 4,144,370 | 3/1979 | Boulton | 428/299 |
| 4,217,901 | 8/1980 | Bradstreet et al. | 604/368 |
| 4,648,876 | 3/1987 | Becker et al. . | |
| 4,657,538 | 4/1987 | Becker et al. . | |
| 4,773,905 | 9/1988 | Molee et al. | 604/378 |
| 4,781,711 | 11/1988 | Houghton et al. . | |
| 4,804,379 | 2/1989 | Toth et al. . | |
| 4,808,467 | 2/1989 | Suskind et al. | 428/301 |
| 4,831,098 | 5/1989 | Watanabe et al. . | |
| 4,863,450 | 9/1989 | Friese | 604/370 |
| 4,908,026 | 3/1990 | Sukiennish et al. | 604/378 |
| 4,936,839 | 6/1990 | Molee et al. | 604/378 |
| 5,188,624 | 2/1993 | Young, Sr. et al. | 604/358 |
| 5,197,959 | 3/1993 | Buell | 604/378 |

FOREIGN PATENT DOCUMENTS

| | | | |
|---|---|---|---|
| 522749 | 4/1956 | Canada | 604/385.1 |
| 884608 | 11/1971 | Canada . | |
| 0 304 957 A2 | 3/1989 | European Pat. Off. . | |
| 1 919843 | 11/1969 | Germany . | |

Primary Examiner—Robert A. Clarke

[57] ABSTRACT

In absorbent products, such as sanitary napkins, discreet areas of dry fibrous materials such as fluid-repellent materials are precisely placed in various planes within the product so as to provide barriers to bodily fluid leakage from the product. In a preferred embodiment, hydrophobic fibers are placed around the periphery of a central absorbent area of an absorbent product to discourage and/or prevent side or end leakage from the product.

44 Claims, 4 Drawing Sheets

SELECTIVE PLACEMENT OF ABSORBENT PRODUCT MATERIALS IN SANITARY NAPKINS AND THE LIKE

This is a continuation, of application Ser. No. 07/970,532, filed Nov. 2, 1992 abandoned, which is a continuation of Ser. No. 879,081, filed May 1, 1992 abandoned, which is a continuation of Ser. No. 717,166, filed Jun. 17, 1991 now abandoned, which is a continuation of Ser. No. 498,017, filed Mar. 27, 1991 now abandoned, which is a continuation-in-part of Ser. No. 334,960, filed Apr. 14, 1989 now abandoned.

BACKGROUND OF THE INVENTION

Field of the Invention

This invention relates to products useful in the absorption of body fluids, such as sanitary protection products, adult incontinence products, diapers, wound dressings and the like. More particularly, this invention relates to absorbent products which contain a means for resisting the transmission of body fluids from the central absorbent element of the product to the body or garments of the wearer of such a product.

CROSS-REFERENCE

This is a continuation-in-part of U.S. application Ser. No. 334,960, filed Apr. 4, 1989. This application also claims priority based on Great Britain application Ser. No. 8911772.5, filed May 23, 1989.

PRIOR ART

One of the major problems inherent in absorbent products has been that bodily fluids absorbed by such absorbent products tend to follow pathways and run off such products and/or fail to remain contained within an absorbent product. In the case of sanitary protection products, this results in menstrual fluid overflowing the absorbent product and staining a wearer's undergarment and/or outergarments. Various approaches have been taken in the past to remedy this situation. For example, flaps have been utilized to protect and wrap around a wearer's undergarment in order to prevent staining from the sides of a sanitary protection product. However, such flaps do not protect the end portions of such sanitary protection products from leaking. In a related patent application, (U.S. Ser. No. 190,803, filed May 6, 1988, PPC 310) repellent fibers have been placed at the transverse ends of a flapped or winged sanitary protection product. However, this design relates only specifically to winged sanitary protection products. Winged products are inconvenient as they require additional work by the wearer to attach them to undergarments. They are also more expensive to make due to the additional adhesive and release paper which must be placed on the wing portions of the product and due to the high level of waste typically associated with such processes.

In U.S. Pat. No. 4,015,604 (Csillag), issued Apr. 5, 1977, an absorbent product is provided with side leakage control means comprising a narrow longitudinally extending zone along each side edge of the product but spaced away from each of the side edges. This zone is impregnated with a liquid hydrophobic material from the garment facing surface to the body facing surface of the product. The extreme longitudinal edges of the absorbent element are free of the impregnation. Cilag merely applies hydrophobic impregnate to a hydrophilic pad as the pad passes through the manufacturing equipment. This can result in uneven placement of hydrophobic material and does not protect the pad wearer from staining at the extreme edges of the pad which are not hydrophobic. In addition, the process according to Cilag does not guarantee that a uniform coating of repellant is applied. This is also a wet process which tends to have more problems related to machine efficiency and microbial contamination issues.

Canadian Patent No. 884,608 issued Nov. 2, 1971, (Levesque) relates to treating the edges of a sanitary napkin product with hydrophobic material in order to prevent side leakage. In accordance with Levesque, the absorbent layer in the zone of the edges of the absorbent is rendered hydrophobic while being maintained in a gas and moisture vapor permeable condition. The hydrophobic zone may be coated with a liquid repellent composition or chemically modified to render the fibers hydrophobic. However, such chemical transformation of hydrophilic fibers into hydrophobic fibers may be imprecise and may not be particularly accurate. This can result in uneven and/or inconsistent presence of hydrophobic fibers. This leads to a lack of uniformity of the distribution of fibers in the fibrous structure which is desired to be rendered hydrophobic. Such lack of uniformity may lead to failure of the fibers to repel body fluids. Thus, there is a need for a sanitary napkin which has a consistent and precise availability of different kinds of fibers and/or materials which can act in a napkin to provide greater protection for the individual wearing such napkin or absorbent product. This leads to a lack of uniformity of the distribution of fibers in the fibrous structure which is desired to be rendered hydrophobic. Such lack of uniformity may lead to failure of the fibers to repel body fluids.

SUMMARY OF THE INVENTION

This invention relates to sanitary protection and absorbent products, such as diapers, incontinent devices and wound dressings and the like, which have fibers and/or other materials specifically placed in particular areas of said products in order to fulfill a particular function as desired or needed. The invention also relates to absorbent products in which dry fibers or other absorbent or repellent or repellent-treated materials have been selectively and accurately placed in strategic positions in a manner so as to maintain the stability of a product containing two or more distinct fibers or material zones, as well as performing other functions, such as repellency, superabsorption and the like. A density gradient for absorption may also be created. In addition, this invention relates to a method for treating fibrous materials to enhance their fluid-repellency and, in particular, to enhance their repellency to menstrual fluids, and to the repellent materials so made. By providing discreet zones of material, a uniform distribution of selected materials is made so as to increase its effectiveness. It also relates to a type of fiber material with defined properties which enables effective repellency of body fluids.

It is, therefore, an object of this invention to provide the selective placement of repellent fibers in a sanitary protection product in order to improve protection by reducing side and end leakage.

It is another object of this invention to increase the absorbent capacity of a sanitary napkin by substantially reducing staining and side and end failure.

It is a further object of this invention to reduce the occurrence of side and end failures of sanitary protection products when such products have been improperly placed or shift during use.

A further object of this invention is to create a softer, drier, more resilient napkin edge that is resistant to collapse under wetting conditions.

Another object of this invention is to provide a sanitary protection product which can be made using a dry, cureless process without using liquids and curing devices such as ovens, microwave products and the like.

Yet another object of this invention is to provide an absorbent product in which superabsorbents or other materials may be placed so as to enhance the absorbent capacity of the absorbent product without deformation, instability and/or wet collapse. This is accomplished by means of enhanced fluid containment or fluid management designs for improved absorbent pulp efficiency.

A further object of this invention is to define the properties of fluid-repellent fiber which will provide adequate resistance to menstrual fluid.

A further object of this invention is to provide a method for enhancing the fluid-repellency of fibrous materials and, in particular, to provide fibrous materials for use in catamenial products which are suited for repelling menstrual fluids.

Additional objects of this invention will become apparent through its description.

DETAILED DESCRIPTION OF THE PREFERRED EMBODIMENTS

In one preferred embodiment of the product of this invention, a sanitary napkin product is provided which contains both hydrophobic and hydrophilic fibers, the hydrophobic fibers being placed in a particular configuration which enhances the stability, or integrity, and efficiency of the entire product.

Figure 1:
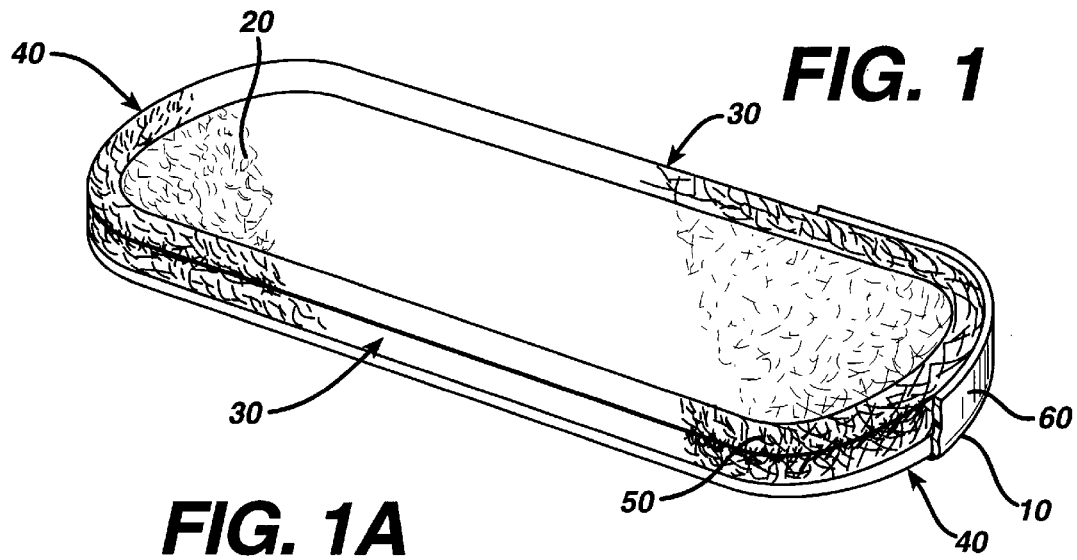
FIG. 1 is a perspective view of a sanitary napkin according to this invention having hydrophobic or repellent portions selectively placed therein.

The repellent fibers may be placed in a configuration around the periphery of a napkin as depicted in FIG. 1. Such a napkin has undergarment facing surface 10 and body facing surface 20 as well as longitudinal edges 30 and transverse ends 40. Hydrophobic pulp fibers 50 may be placed around the periphery of the product to a depth from body facing surface 20 to garment facing surface 10 of less than 100% of the height of the product. Hydrophobic pulp 50 forms a hydrophobic barrier portion. This hydrophobic barrier portion forms a body-fluid repellent border or area which aids in containing fluid within the absorbent, hydrophilic areas. Preferably, the hydrophobic barrier portion extends between about 50 and 95%, and more preferably between about 70 and 80%, of the height of the product from body facing surface to the undergarment-facing surface of the product.

The hydrophobic barrier portion thus cuts into the center absorbent area so that the absorbent area, when viewed in cross-section, is in the approximate form of a "T", the base of which forms the body-facing side of the absorbent product. Although the extension of the border to 100% of depth is achievable, it may significantly decrease the stability of the product, as the materials will tend to separate more easily within the process and in use. Use of heat activated elements may help to achieve up to 100% depth without loss in stability. Constructing the hydrophobic repellent border such that its height is approximately 70 to 80% of the height of the product allows for better fiber entanglement between the hydrophobic and hydrophilic fibers and stability required to maintain a unitized structure throughout production and use. This structure also makes more hydrophilic fibers available for absorption. The repellent barrier portion may also extend higher than the height of the hydrophilic absorbent core, so as to provide a gasket-like edge surrounding the absorbent core. This can result in a structure which physically discourages the movement of fluid outside the edges of the napkin. Both the hydrophilic and hydrophobic areas may contain thermoplastic fibers such that, upon exposure to heat or other energy sources, the fibers will adhere to each other and the pad will become a unitized stable whole.

Figure 1A:
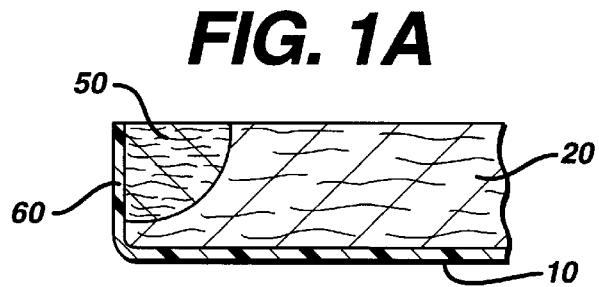
FIGS. 1A is a partial cross-sectional view of sanitary napkins according to this invention having hydrophobic or repellent portions selectively placed therein.

The hydrophobic barrier portion of the pad should be at least 1/16 wide at the face of the product. It may taper off below the surface, as shown in FIG. 1A, so as to provide greater absorbent capacity in the core where absorbent capacity is needed.

Preferably, a polymeric barrier film is applied to the garment-facing side of the absorbent core in order to protect the garment from leakage from the absorbent core. The barrier film may also be wrapped around the side portion of the napkin in order to provide an extra barrier adjacent to the hydrophobic/hydrophilic barrier. Wrapping the barrier film completely around the napkin with the exception of the body-facing side of the napkin product will also aid in maintaining structural stability.

In lieu of a polymeric barrier film, a repellent or hydrophobic fiber blanket may be applied to the garment-facing side of the absorbent core to protect the wearer's garment from leakage from the absorbent core.

Under normal conditions, fluid wicks in every direction, toward the bottom, sides and ends of the pad, radially. Normal forces of use and compression accelerate this wicking. When fluid reaches a repellent edge in the products of this invention, the edge resists further lateral flow of fluid towards the sides of the napkin. Normal capillary action then allows fluids to wick preferentially toward the ends of the napkin, resulting in the better use of the central absorbent core and capacity available therein. In conventional rectangular sanitary protection pads, napkin leakage occurs mostly when fluids reach the napkin sides or one end of the pad and stain the undergarment before the absorbent is efficiently used over the full pad length.

Of course, placement of the hydrophobic portion of the fibers need not be limited to a so-called "racetrack" design which follows around the periphery of the napkin. Additional configurations include a series of "stripes", or channels located along the longitudinal axis of the napkin. Such hydrophobic fibers may be placed also along the longitudinal sides or edges of the napkin. Alternatively, the repellant zones may be intermittently spaced in the body of the pad in patterns desired by one of ordinary skill in the art.

The hydrophobic and hydrophilic pulp are preferably colored differently. For example, the hydrophilic pulp may be white and the hydrophobic pulp may be blue.

Figure 2:
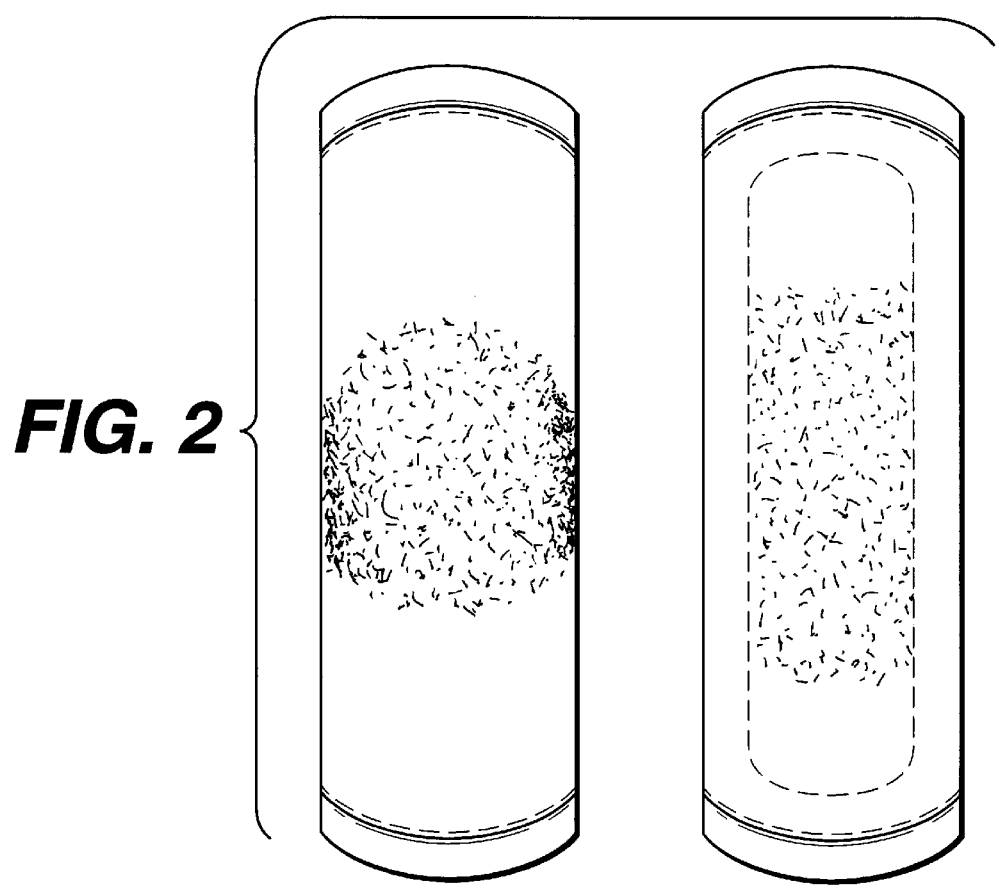
FIG. 2 is a top view of STAYFREE MAXIPAD a and a selective placement menstrual pad according to this invention b illustrates shows the fluid wicking behavior of both pads.

FIG. 2 illustrates the difference in fluid wicking behavior in which a STAYFREE MAXIPAD has been exposed to the deposition of 50 cc of synthetic menstrual fluid and subjected to the placement of a 6 kg load over the pad surface for 30 seconds. The same treatment has been accorded the selective placement pad. FIG. 2 illustrates that the synthetic menstrual fluid tends to stay in the middle and radiate in a circular area of the STAYFREE pad, thus increasing the possibility of side leakage. In the selective placement pad of this invention, the synthetic menstrual fluid flowed along the longitudinal axis of the pad and was stopped from overflowing the sides of the pad.

Thus, it can be seen that the repellent fiber edge resists wetting, although fluid may be temporarily forced into the interstitial spaces in the edge when subjected to compression. When such forces are released, the absorbent section of the product will reabsorb the fluid and it will be prevented from leaking over the sides or through the repellent fiber section of the pad and therefore prevent staining.

Figure 3A:
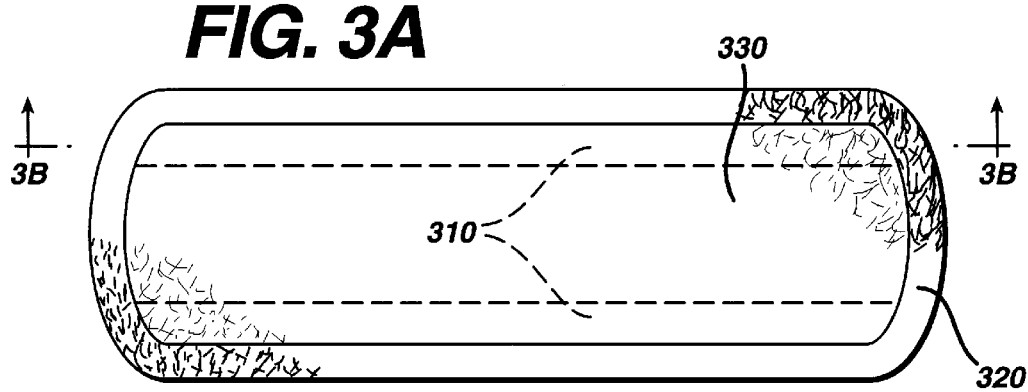
FIG. 3A is top view of a sanitary napkin of this invention incorporating superabsorbent materials.
Figure 3B:
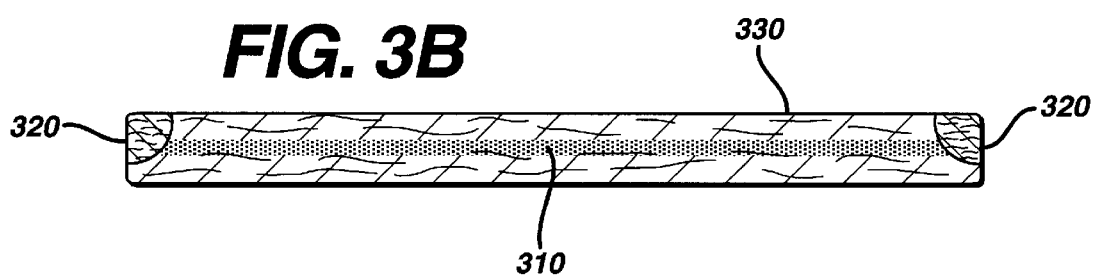
FIG. 3B is a longitudinal cross-section of the same napkin.

Another preferred embodiment of the product of this invention is illustrated in FIGS. 3A and 3B. Using the concepts discussed above with respect to placing repellent fibers in a specific configuration, an absorbent product also may be enhanced by strategically placing superabsorbent materials within the structure. Superabsorbent materials 310 can be effectively used to reduce leakage from areas of saturated absorbent pulp which can cause staining if subjected to sudden changes in pressure or forces exerted on the pad. For example, superabsorbent materials 310 may be placed with a powder spray between the repellent fiber zones 320 and absorbent fiber zones 330. This design permits the repellent fibers to resist lateral fluid wicking and allows the superabsorbent material time to absorb and retain large volumes of fluids. In other circumstances such as those in the prior art, superabsorbent materials can be less than totally effective because they are subjected to large amounts of fluid which cause gel blocking. With the advent of the novel products of this invention, superabsorbent material may be used in a much more effective way to be placed and to provide time for absorption.

Figure 4A:
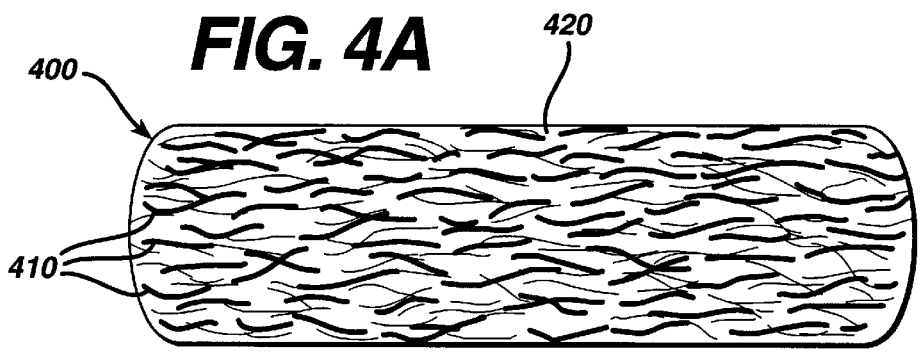
FIG. 4A is a top view of a central absorbent portion of a sanitary napkin, formed from a pulp and heat-activated fiber blend.
Figure 4B:
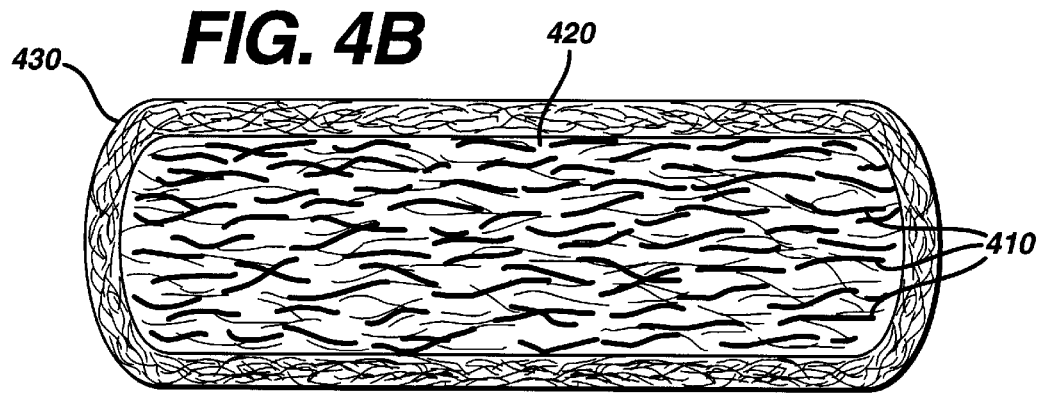
FIG. 4B is a top view of a sanitary napkin according to this invention incorporating the central absorbent portion illustrated in FIG. 4A and a repellant pulp barrier.

FIGS. 4A and 4B illustrate sanitary protection product 400 having a zone containing heat-activated stabilizing elements 410. The entire napkin or the central absorbent portion 420 alone or the repellent portion 430 alone of napkin 400 contains heat activated fiber, for example, PULPEX™ fiber available from Hercules Corporation, which is incorporated with other pulp fibers and may be exposed to thermal energy and stabilized. Repellant pulp 430 may be placed around this absorbent pulp, as illustrated in FIG. 4B, creating a discrete interface between the repellent and absorbent pulp. When the napkin 400 is heat activated, the repellent pulp will bond to the absorbent pulp at the interface to form a unitized structure. This structure may then be heat calendared or a heat active table cover material can be heat calendared or heat embossed into the core in order to form a stable structure able to resist deformation. This would also allow the depth of the repellent pulp to be increased to 100% of the pad depth without sacrificing product stability.

Figure 5:
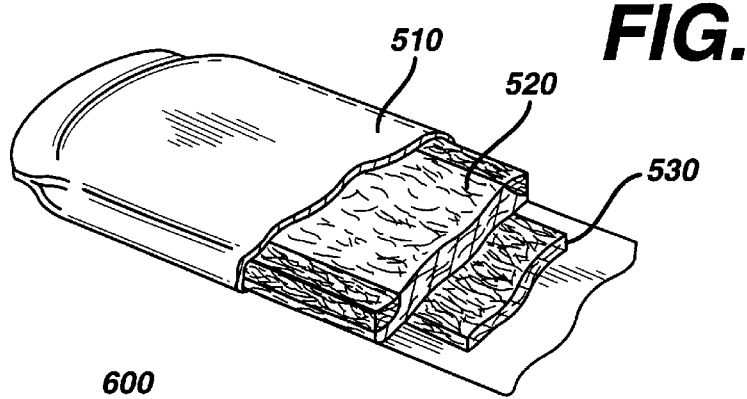
FIG. 5 is a perspective view of a sanitary napkin according to this invention in which the central absorbent section comprises both an uncompressed section at the body facing side and a compressed high density layer on the undergarment facing side.

FIG. 5 illustrates another preferred embodiment of the product of this invention in which central absorbent section 510 has a low density, uncompressed section 520 at the body facing side and a compressed high density layer 530 below the top section on the undergarment facing side. Compressed layer 530 may provide a higher degree of stability in use, however, compression of pulp in this layer may sacrifice some of its absorbent capacity. Thus, a highly absorbent material in soft board form may be provided in lieu of or in addition to compressed pulp layer 530 in order to provide both stability and higher capacity. For example, compressed peat moss board such as that described in copending application number (J&J 1238) may be placed as the lowest layer of this construction. This provides a high capacity fluid drawing "pulp" which draws fluid into the interior of the product leaves less fluid on the surface adjacent to the body facing side.

Figure 6:
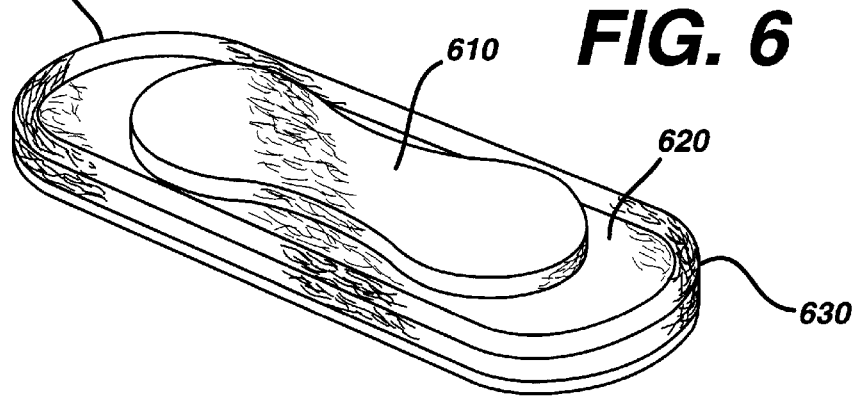
FIG. 6 is a perspective view of a sanitary napkin according to this invention which has been shaped in a three-dimensional manner in order to improve contact between the wearer's body and the product.

FIG. 6 illustrates sanitary protection product 600 which has been shaped in a three-dimensional manner in order to improve contact between the wearer's body and the product. This provides a means 610 to capture menstrual fluid in the product quickly as it is exuded from the body and to reduce the probability of staining undergarments. The incorporation of three-dimensional shaping in the selective placement products of this invention (for example the raised-center design illustrated in FIG. 6) enhances their design by delivering the fluid into the napkin structure where it is maintained within absorbent section 610. Since absorbent sliver 620 is surrounded by the repellent fiber material 630, the fluid does not leak from either the sides or the ends. Thermoplastic materials such as PULPEX™ in the absorbent and/or repellent pulp sections of the napkins of this invention provide ease in achieving these designs. The application of heat and pressure to compress the peripheral area and leaving the uncompressed section to project out of the napkin for improved body contact can be achieved in this manner. Upper portion 610 may be formed as an integral part of section 620; or, it can be formed as a separate shaped sliver and placed on top of the bottom sliver. Alternatively, it can be formed as a combination of the above and calendared.

Figure 7A:
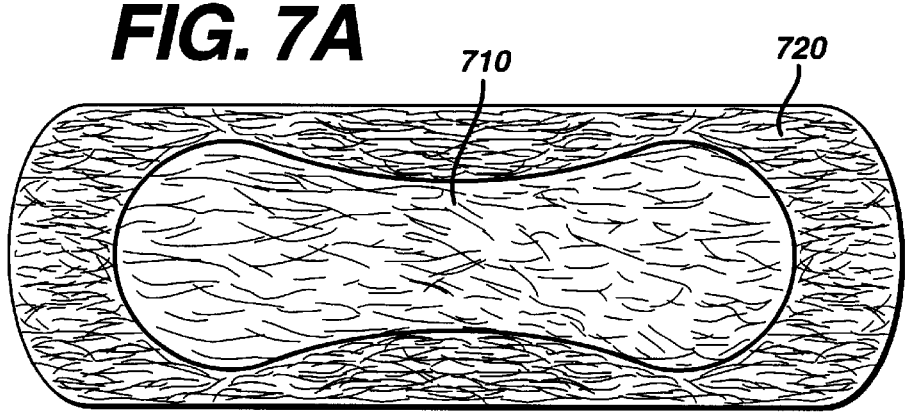
FIGS. 7A and 7B are top views of sanitary napkins according to this invention exhibiting different patterns of absorbent and repellent zones.
Figure 7B:
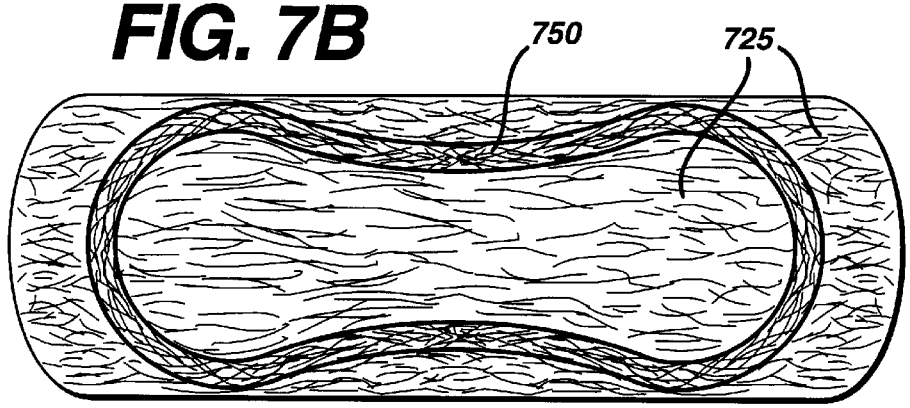

Likewise, the repellent zone of the product depicted in FIG. 1 may be shaped in an hourglass or other aesthetic and functional shape in order to provide additional protection in certain areas where it is required. This provides a means for the consumer to discern the availability of the repellent edge. Thus, FIG. 7A provides an illustration of a preferred embodiment where central absorbent portion 710 is shaped in an hourglass configuration whereby repellent zone 720 is wider at the center edges at the central portion of the napkin so as to provide additional protection where it is most needed and a resistance to the lateral flow of fluids within the napkin. FIG. 7B illustrates another embodiment in which repellent zone 750 is shaped in an hourglass pattern within the central absorbent zone having absorbent pulp fibers 725. Shaping of the absorbent pads can be achieved with the use of contoured dies or molds in the vacuum forming device. The advantages of such a shaped zone include reducing the area of surface wetness which can contact the body and limiting the effects of wicking and failure at the napkin sides.

Figure 8:
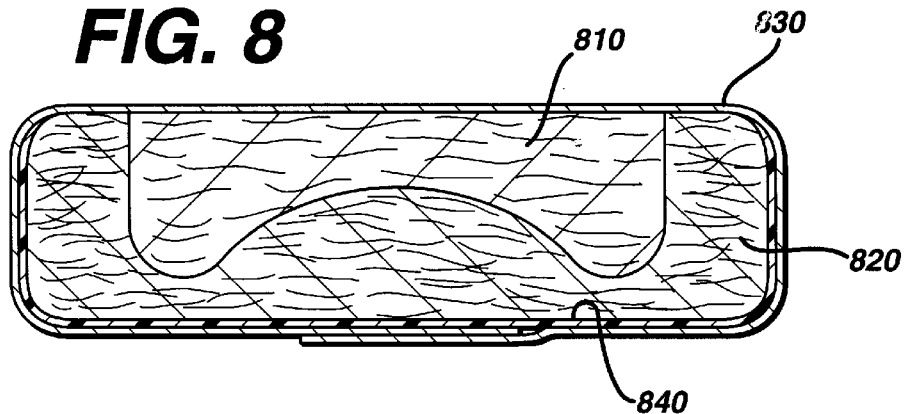
FIG. 8 is a cross-sectional view across the width of a sanitary napkin according to this invention illustrating an embodiment directed to reducing wet collapse of the napkin structure.

FIG. 8 illustrates another preferred embodiment of the sanitary protection products of applicant's invention. This embodiment is directed to promoting the stability of wet pulp structures after compression and providing resilience to such structures. In sanitary protection products or the like where ground communitive grade wood pulp or cellulose is used as the primary absorbent medium, wet collapse of the absorbent begins at the point of initial fluid deposition and continues over the available surface area with increasing deposits of fluid and subsequent wicking within the absorbent structure. Faster wicking and subsequent wet collapse are accelerated with the various forces normally applied to a pad in dynamic use. This wicking typically occurs along paths of least resistance to the fluid. As illustrated by FIG. 8, a repellent treated pulp fiber blanket in the form of a "W" 820 aids in resisting wet collapse in the center 810 and peripheral edges 830 of the product by maintaining a critical thickness at the center of the pad for enhanced body contact after initial wetting of the pad and, at the extreme edges of the pad, for reduced leakage by containing the fluid within the pad. This design also enhances absorbence by channeling fluids along the napkins length within the valleys of the "W" section. Fluid is absorbed in the center of the pad where the depth of absorbent pulp is sufficient for absorption and wicking. Wet collapse is reduced at the center and ends of the pad by virtue of the presence of the nonwettable pulp. Materials which wick fluids very well may also be placed in the central portion of the "W" conducive to wicking the material along the longitudinal axis of the napkin. A breathable barrier 840 may be placed below the "W" section in order to provide a breathable product construction. The nonwettable pulp will provide an initial barrier, which is also breathable, and the second barrier, which may be composed of a breathable film or repellant treated tissue layer, provides another protective layer to prevent staining and leakage. The higher the density of this nonwetting pulp, the lower its porosity and the higher its resistance to strikethrough of fluids under pressure in a breathable construction.

Figure 9:
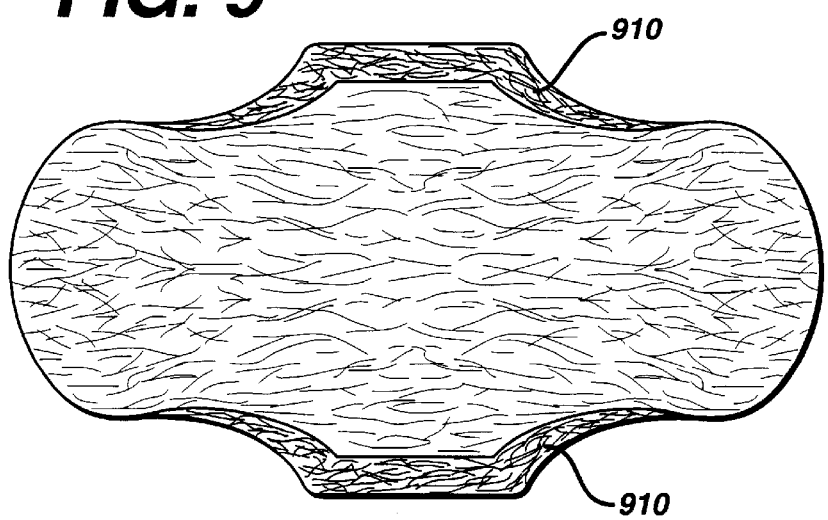
FIGS. 9 and 10 are top views of sanitary napkins according to this invention in "winglet" form.
Figure 10:
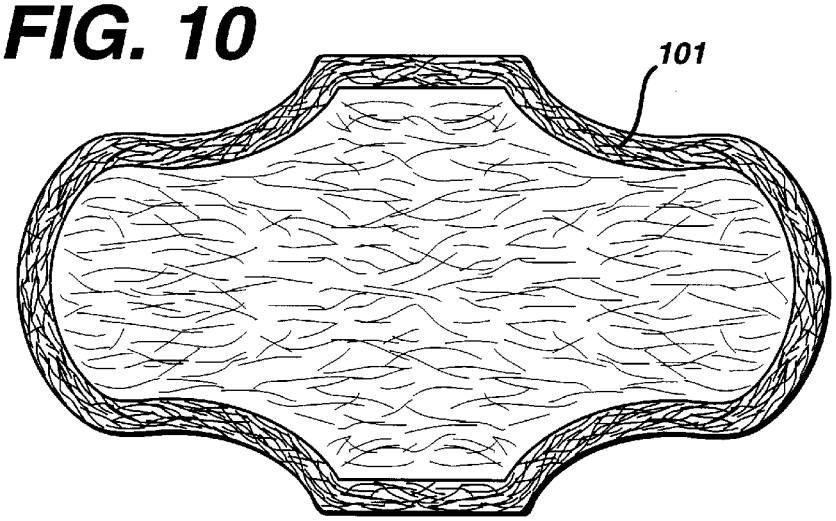

The concepts of this invention may also be used in order to provide a "winglet" type sanitary protection product such as that illustrated in FIG. 9 and FIG. 10. In general, the wing portions of "winglet" type napkins are designed to spread over or around the crotch of the wearer's undergarment and enhance stain-protection of that garment. Winged-type sanitary protection products with flimsy wings may become saturated with fluid and wick fluid onto the thighs of the wearer. Moreover, the wings tend to collapse under exposure to fluid and fail to contain the fluid within the central absorbent element of the product. Placing repellent resilient fiber in the winglet portions 910 of such a pad and/or completely around the periphery 101 of such a pad provides the advantage of placing a protective barrier around the winglet area which reduces leakage from the wing onto undergarments, the body, or outer clothing. Moreover, it provides a more resilient product construction. The contoured placement of the repellent pulp in the wings allows a wider absorbent pulp coverage at the center of the pad where it is most needed. Thus, fluid entering the wings can be absorbed in larger amounts due to the presence of absorbent pulp within the repellent pulp border.

Of course, the concepts of the product of this invention may be applied in other ways to provide layered products, in which layers of different kinds of material may be selectively placed within an absorbent core so as to maintain a stable construction. For example, aesthetically pleasing high quality white absorbent pulp may be placed in a top layer facing the body and covering unbleached or semi-bleached pulp fiber or other less aesthetic fiber for the purpose of lowering costs without sacrificing the performance or visual attributes of the napkin. Alternatively, hydrophobic fibers may be placed over an absorbent core to reduce surface staining, in order to increase softness and comfort and enhance surface and napkin resilience. In another embodiment, a low density layer of pulp may be formed over a higher density pulp layer in order to aid in wicking fluid from the facing to the high density layer, thus leaving a drier surface. A low wicking fiber may also be placed toward the body facing surface over a high wicking fiber. A soft, resilient layer of fibers may be layered over an absorbent core, or a blend of long and short fibers may be covered over an absorbent core to improve stability. Absorbent and heat activated fibers may be blended in a layer to enhance overall pad stability. Thermoplastic fibers and other fibers covering an absorbent core may be blended to form a cover. This construction is less costly than using web or film cover and improves the cover-to-core contact without the use of adhesives. In addition, a hydrophobic, fibrous layer, acting as a "breathable" fluid barrier may be layered under an absorbent batt. This barrier may be used in conjunction with "breathable" barrier film, superabsorbents or hydrophobically treated nonwoven inserts.

The specific embodiments of this invention described above utilize selectively placed hydrophobic or fluid-repellent areas in absorbent products also incorporating hydrophilic or fluid-absorbing materials. Suitable hydrophobic or fluid-repellent materials which can be used for this purpose include polyester, polyethylene, polypropylene and bicomponent-type fibers. Bicomponent fibers consist of a core composed of a synthetic fiber (e.g., polyester) and an outer sheath having a lower melting temperature (e.g., polyester or polyethylene), which can be heat-activated to enhance the stability of a fibrous structure. Examples of bicomponent fibers useful in the products of this invention are Enka™ available from American Enka Company or Chisso™ fibers available from Chisso Company of Japan. Alternatively, and preferably, due to cost and process considerations, conventional absorbent materials such as pulp can be treated via a repellent sizing process to yield repellent materials useful in these embodiments. For example, a pulp material can be sized with a cationic repellent (e.g., fatty acid ketene dimer, such as Aquapel 360XC, available from Hercules, Inc., Wilmington, Del.) or subjected to treatment with silicone resins or fluorocarbons, to yield a repellent material suitable for use in the selective placement absorbent products of this invention. This pre-sizing of an absorbent pulp fiber, which, in the untreated state has no resistance to absorption and wicking of body fluids, gives it repellent properties to resist or substantially prevent absorption or wicking of said fluids within the products of this invention. In addition to treated wood pulp, hydrophobic materials such as the aforementioned polyester, polyethylenes, polypropylenes, heat fusible fiber and the like can also be used in the illustrated product designs, as they possess similar properties which would allow them to resist absorption and wicking. These fibers can also be chemically sized with repellents to further increase their resistance to fluids.

In addition, hydrophobic materials such as the aforementioned polyester, polyethylenes, etc. can be sized or treated as mentioned above to further lower their critical surface energy. The ability to pretreat materials to enhance their repellency, and the use of vacuum forming capabilities allow one to place repellent fibers virtually anywhere within the X, Y and Z planes of an absorbent product during its manufacture, allowing products to be made with specifically designed fluid flow properties.

The type and variables of the treatment utilized to imbue a material with greater fluid repellency will be adjusted to provide a repellent material with the optimal properties for its intended use. Research has shown that, while the surface tension of water is generally in the range of 69–72 dynes/cm., that of menstrual fluid is in the range of less than 45–57 dynes/cm. Therefore, a repellent or hydrophobic material used according to this invention in an absorbent catamenial product should preferably have a critical surface energy less than about 44 dynes/cm. Otherwise, menstrual fluid will wet the surface and, in the case of conventional materials like pulp, also absorb and wick into the pulp. By the same token, it would be within the skill of one skilled in the art to determine the ideal critical surface energy for other absorbent products, e.g., diapers, incontinent products, and the like.

For example, repellent treated pulp, Enka bicomponent fibers washed with methanol to remove surfactants, polypropylene and polyester fibers were measured for critical surface energy. The fibers had critical surface energy measurements as follows:

Critical Surface Energies For Certain Fibers

| Fiber Type (dynes/cm) | Critical Surface Energy |
|---|---|
| Repellent treated pulp | 28–33 |
| Enka bicomponent | 28–33 |
| Polypropylene | 28–33 |
| Polyester | 43 |

Repellent fibers suitable for use in selective placement catamenial products according to this invention can be made by sizing a pulp material with adequate (cationic) repellent at concentrations of at least about 0.19% on total weight of pulp. Table 1 provides data showing the repellency of untreated pulp and repellent-treated pulp to synthetic and actual menstrual fluid. High and low viscosity synthetic fluids were prepared by dissolving a water soluble polyacrylamide polymer in isotonic phosphate buffer (pH 7.4). Low and high viscosity fluids contain 0.15% and 0.4% polymer, respectively, and have viscosities of 30 cps and 280 cps, respectively. A germicide is used to prevent bacterial growth.

TABLE 1

Repellency of Pulp vs. Synthetic Menstrual Fluid

| Concentration (% total wt.)* | Type I[1] Synthetic Menstrual Fluizd | Type III[2] Synthetic Menstrual Fluid | Menstrual Fluid[3] |
|---|---|---|---|
| 0 | wetting | wetting | wetting |
| 0.11 | wetting | no wetting | no wetting |
| 0.19 | no wetting | no wetting | no wetting |
| 0.26 | no wetting | no wetting | no wetting |
| 0.34 | no wetting | no wetting | no wetting |

*Repellent is Aquapel 360XC from Hercules, Inc.
[1]Type I synthetic menstrual fluid is formulated with physical properties (surface tension, viscosity, specific gravity) consistent with that of whole blood. This would represent the worst case type of discharge during normal menstrual flow in which fluid viscosities are lowest and other fluid properties are consistent with that of whole blood.
[2]Type III synthetic menstrual fluid is formulated with a viscosity that is much greater than that of whole blood and represents the very viscous, gelatinous material common to menstrual discharges.
[3]Menstrual fluid was collected in-vivo and pooled to represent a typical fluid discharge.

It has been shown that the visco-elastic properties of menstrual fluids will vary greatly within a cycle and, generally, within any given population. The data presented in Table 1 indicate that 0.19% sizing by weight is the minimum level at which the hydrophobic material can be expected to repel the full range of menstrual fluids, independent of viscosity. Preferably, the pulp should be treated with adequate repellent to provide a product having between about 0.19% and 0.34% repellent per total weight of the product.

To reduce the static potential of the pretreated repellent pulp or the high cost contributed by use of either a pretreated repellent pulp or hydrophobic fiber, it may be desirable to blend the pretreated repellent pulp or other hydrophobic fiber with absorbent pulp. The data presented in Table 2 indicate that effective repellency versus menstrual fluid (surface energy of less than 45 dynes/cm) can be maintained if the pretreated pulp or hydrophobic fiber is mixed with percentages of absorbent pulp or fiber up to 50%. The data in Table 2 were obtained by applying fluids of known surface tensions to the surface of the repellent treated material. Starting with a fluid with a relatively high surface tension, fluid drops were applied to the test substrate until the material began to wet out. The critical surface energy of the substrate was estimated to be equal to the surface tension of the fluid where initial wetting was noted.

TABLE 2

Surface Energy of Hydrophobic/Hydrophilic Pulp Fiber Blends

| Blend (%) Hydrophobic*/Hydrophilic Pulps | Critical Surface Energy dynes/cm |
|---|---|
| 25/75 | 58 |
| 50/50 | 43 |
| 75/25 | 37 |
| 100/0 | 32 |

*Hydrophobic portion treated with 0.34% repellent by weight.

One must consider not only the critical surface energy of the repellent or hydrophobic material utilized in an absorbent product, but also the density of the material. Greater hydrostatic pressures are required to penetrate repellent versus absorbent pulp. This is shown by Table 3 in which the resistance of pulp to fluid flow is measured as a function of repellent treatment. Samples were evaluated at two densities, 0.5 g/cc and 0.15 g/cc. The higher density pulp was tested in a Flow Through Tester from TRI. In this test, water is forced through the pulp under pressure and the resistance to flow is measured via a pressure transducer. Since the lower density pulp fluff is much more sensitive due to its more open or porous fibrous structure, a more sensitive technique was employed to measure resistance, namely, a Buoyancy Tester from TRI. The Buoyancy Tester allows the automatic monitoring of liquid penetration and breakthrough under constant or variable hydrostatic heads. In this test, if one side of the fabric is placed in contact with liquid in a reservoir, the buoyancy force will decrease systematically as liquid displaces air within the fabric pores.

TABLE 3

Resistance of Pulp to Fluid Flow

| % of Sizing* | Critical Surface Energy (dynes/cm) | Resistance, psi 0.5 g/cc | Resistance, psi 0.15 g/cc |
|---|---|---|---|
| 0 | 70 | 0 | 0 |
| 0.11 | 58 | 3.2 | 0.045 |
| 0.19 | 34 | 5.75 | 0.24 |
| 0.26 | 33 | 6.08 | 0.24 |
| 0.34 | 32 | 6.16 | 0.24 |

*Aquapel 360XC, Hercules, Inc.

The data in Table 3 indicate that, as the repellent amount increases, critical surface energy (wettability) decreases and the resistance to fluid flow increases. It also indicates that barrier protection for this particular repellent treatment is maximized at a relatively low add-on (between about 0.19 and 0.26% repellent).

As shown above, the ability of a fibrous material zone or layer to resist fluid flow within the products of this invention is a function of each individual fiber's ability to repel fluids as well as the porosity or density of said zone within the product. Individual fibers must first possess sufficient properties to resist menstrual fluids, by virtue of their inherent hydrophobic properties and/or repellent treatments such as those already discussed, and as measured as a function of critical surface energy. Given any fiber with a critical surface energy of less than 45 dynes/cm and preferably less than 40 dynes/cm, resistance to menstrual flow can then be enhanced by increasing the density of the material one or layer containing said fibers.

Tables 4A and 4B below examine the impact of increasing densities on flow resistance for two different fibers with similar hydrophobic properties. Table 4A sets forth the raw data obtained by increasing the density of the fibrous mass made by the conjugation of the fibers. Table 4B represents the linear comparison between the two materials—a repellent treated pulp and a washed Enka Bicomponent (polyester core, polyethylene sheath) fiber. Each fiber recorded critical surface energies of less than 33 dynes/cm and greater than 28 dynes/cm.

TABLE 4A

Resistance of Pulp to Fluid Flow

| Density(g/cc) | Resistance (psi) Repellent Pulp | Resistance (psi) Washed Enka |
|---|---|---|
| 0.39 | 0.22 | |
| 0.37 | 0.176 | |
| 0.36 | 0.264 | |
| 0.23 | 0.22 | |
| 0.23 | 0.176 | |
| 0.29 | 0.176 | |

TABLE 4A-continued

Resistance of Pulp to Fluid Flow

| Density(g/cc) | Resistance (psi) Repellent Pulp | Resistance (psi) Washed Enka |
|---|---|---|
| 0.17 | 0.132 | |
| 0.19 | 0.176 | |
| 0.16 | 0.132 | |
| 0.06 | 0.033 | |
| 0.07 | 0.022 | |
| 0.05 | 0.044 | |
| 0.39 | | 0.363 |
| 0.33 | | 0.186 |
| 0.32 | | 0.226 |
| 0.3 | | 0.242 |
| 0.23 | | 0.147 |
| 0.19 | | 0.142 |
| 0.05 | | 0.039 |
| 0.05 | | 0.035 |
| 0.05 | | 0.035 |

TABLE 4B

Flow Resistance of A Fibrous Structure

| Density(g/cc) | Resistance (psi) Repellent Pulp | Resistance (psi) Washed Enka |
|---|---|---|
| 0.05 | 0.082 | 0.089 |
| 0.1 | 0.15 | 0.147 |
| 0.15 | 0.217 | 0.204 |
| 0.2 | 0.285 | 0.261 |
| 0.25 | 0.353 | 0.319 |
| 0.3 | 0.421 | 0.376 |

Tables 4A and 4B expand on the data presented in Table 3. The same increase in fluid flow resistance is found with increasing densities for both fibers having similar hydrophobic properties. Typical densities of the hydrophobic material zones within the products of this invention are between about 0.05 and about 0.1 gm/cc. Within this range of densities no individual value of flow resistance for either fiber falls below 0.02 psi. Based upon the linear relationship established between resistance to fluid flow and density for the data obtained, set forth in Table 4B, normal resistance to flow would be anticipated to average between about 0.08 and about 0.15 psi and to have no individual values less than about 0.02 psi independent of fiber type used, given that the material has a critical surface energy less than the lowest surface tension of normal menstrual fluid (45 dynes/cm) and a material density between the densities of about 0.05 and about 0.10 gm/cc to be used in the majority of the product design executions of this invention. To achieve higher densities for some of the synthetic hydrophobic fibers for use in the products of this invention, it may be necessary to apply heat to the sample under compression.

Fibers pretreated to enhance their repellency are also useful in enhancing the structural stability of the absorbent products in which they are incorporated. As opposed to hydrophilic or absorbent fibrous layers which tend to readily absorb fluids and collapse in the wet state, hydrophobic or pretreated repellent pulp fibrous structures, used according to this invention to provide enhanced fluid management within an absorbent structure, will resist wetting by menstrual and other bodily fluids and thus will not readily collapse in the presence of these fluids. Measureable resistance to wetting and fluid flow through the hydrophobic fibrous structures, and subsequently greater resistance to wet collapse, allows an efficient utilization of absorbent fibers in a repellent fiber/absorbent fiber matrix. Enhanced resistance to wetting and wet collapse is not only dependent on wettability but also on pore size or density of the fibrous structure. Fluids need to be forced under pressure into a repellent-treated or hydrophobic fibrous structure as opposed to an absorbent fiber mat where no force is necessary. The smaller the pore size, the greater the density and the greater the resistance to wet collapse in a dynamic state under pressure.

The sanitary protection products and absorbent products of this invention may be made by hand, by selectively placing materials in the appropriate configurations, or they may be made in vacuum forming equipment, using molds and dies and/or baffles which are capable of directing the different types of materials to be selectively placed in the desired areas. Conventional pulp web generating equipment can also be modified to provide different material zones for similar executions. They may also be made by any other known processes available to those of skill in the art which are capable of achieving the configurations set forth in the foregoing specification.

What is claimed is:

1. An absorbent product comprising a unitized mass of fibers having a body facing side and a garment facing side, said unitized mass of fibers having a discrete bodily fluid-absorbent zone comprising fibers and a bodily fluid repellent zone comprising bodily fluid repellent fibers and disposed at least in part on said body facing side to provide a barrier to bodily fluid leakage; wherein a sufficient number of said fluid repellent fibers are entangled with a sufficient number of said absorbent zone fibers to join said fluid absorbent and fluid repellent zones.

2. An absorbent product according to claim 1 wherein said fluid absorbent zone is formed at least in part from hydrophilic fibers.

3. An absorbent product according to claim 1 wherein said fluid absorbent zone comprises hydrophilic fibers, and wherein at least one of said zones comprises stabilizing elements caused to adhere to said fibers comprising said zone by the exposure of heat to said stabilizing elements.

4. An absorbent product according to claim 1 wherein said fluid repellent zone comprises a repellent treated fiber blanket having a body facing surface cross-section in the form of a "W", a first side of said W facing toward said body facing side of said product, and wherein said fluid absorbent zone comprises hydrophilic pulp fibers placed on said first side of said "W" to form an essentially planar body facing surface.

5. An absorbent product according to claim 1 which comprises a sanitary napkin.

6. An absorbent product according to claim 1 wherein said fluid repellent zone has a resistance to fluid flow when water is forced through said fluid repellent zone under pressure, said flow resistance being at least 0.02 pounds per square inch of fluid pressure.

7. An absorbent product according to claim 1 wherein said fluid absorbent zone is a first fluid absorbent zone, and further comprising a second fluid absorbent zone formed at least in part from superabsorbent material, said second fluid absorbent zone disposed between said fluid repellent zone and said first fluid absorbent zone so as to act as a flow retardant.

8. An absorbent product according to claim 1 wherein said unitized mass of fibers is vacuum-formed.

9. An absorbent product according to claim 1 which further comprises a barrier applied to the garment facing side of said unitized mass of fibers.

10. An absorbent product according to claim 9 wherein said barrier is applied to side edges of the unitized mass of fibers.

11. An absorbent product according to claim 9 wherein said barrier comprises a sheet of material selected from the group consisting of a polymeric film and a hydrophobically-treated nonwoven fabric.

12. An absorbent product according to claim 1 wherein said discrete bodily fluid-repellent zone is disposed at least in part on the body facing side across longitudinal ends of the product.

13. An absorbent product according to claim 1 wherein said discrete fluid absorbent zone comprises hydrophilic fibers and said discrete fluid repellent zone comprises hydrophobic fibers.

14. An absorbent product according to claim 13 wherein said fluid absorbent zone comprises a lower density, uncompressed section at the body facing side of the product and a compressed higher density section below said uncompressed section on the garment facing side of the product.

15. An absorbent product according to claim 13 further comprising longitudinal edges, and wherein said fluid repellent zone is formed in the shape of wings appended to said longitudinal edges.

16. An absorbent product according to claim 13 wherein said hydrophilic and hydrophobic fibers are visibly differentiated by color.

17. An absorbent product according to claim 13 wherein said fluid repellent zone comprises a continuous layer of hydrophobic fibers having a higher density than said fluid absorbent zone, said layer of hydrophobic fibers being placed on said garment facing side of said product.

18. An absorbent product according to claim 13 wherein said hydrophobic fibers comprise fibers selected from the group consisting of polyester, polyethylene, polypropylene and bicomponent fibers.

19. An absorbent product according to claim 13 wherein said hydrophobic fibers comprise absorbent fibers pretreated to render them substantially repellent to bodily fluids.

20. An absorbent product according to claim 19 wherein said hydrophobic fibers comprise pulp fibers pretreated with a cationic repellent.

21. An absorbent product according to claim 13 wherein said fluid absorbent zone has a periphery, and wherein said fluid repellent zone is disposed so as to surround said periphery of said fluid absorbent zone on said body facing side.

22. An absorbent product according to claim 21 wherein in cross-section said fluid repellant zone extends from the body facing side approximately 50–95% of the height of the product.

23. An absorbent product according to claim 21 wherein said hydrophobic fibers are placed around the periphery of said fluid absorbent zone and in cross-section the height of said repellent zone is approximately 70–80% of the height of the product.

24. An absorbent product according to claim 21 wherein said bodily fluid absorbent zone has a cross-section in the form of an inverted "T" having a narrow topside and a wide bottom side, said narrow top side forming an inner portion and said fluid repellent zone forming an outer peripheral portion of said body-facing side of the product.

25. An absorbent product according to claim 21 wherein said fluid absorbent zone is a first fluid absorbent zone, and further comprising a second fluid absorbent zone formed at least in part from superabsorbent material, said second fluid absorbent zone located between said fluid repellent zone and said first fluid absorbent zone.

26. An absorbent product according to claim 21 wherein at least one of said hydrophobic fibers and said hydrophilic fibers comprises stabilizing elements capable of acquiring adherency by the exposure of heat thereto.

27. An absorbent product according to claim 26 wherein the height of said fluid repellent zone is approximately 100% of the height of the product.

28. An absorbent product according to claim 21 wherein said product is shaped such that at least a portion of said fluid absorbent zone extends above said fluid repellent zone.

29. An absorbent product according to claim 13 which comprises a sanitary napkin.

30. An absorbent product according to claim 29 wherein said hydrophobic fibers are not subject to wetting by fluids having a surface tension greater than about 45 dynes/cm.

31. An absorbent product according to claim 29 in which said hydrophobic fibers comprise pulp fibers treated with cationic repellent, such that said cationic repellent comprises between about 0.19 and about 0.34 weight % of the pulp.

32. An absorbent product according to claim 30 in which said fluid repellent zone comprises a blend of hydrophilic fibers and hydrophobic fibers treated with cationic repellent.

33. An absorbent product having a body facing side and a garment facing side, having a discrete fluid absorbent fibrous element and a discrete fluid-repellent fibrous element, made by a process comprising the steps of:
 a) contacting one of said discrete fibrous elements with an effective repellent amount of one or more cationic repellents to form the fluid-repellent element; and
 b) joining said discrete fluid-repellent fibrous element to said discrete absorbent fibrous element so as to form a unitized structure;
wherein a sufficient number of the fibers of said fluid-repellent fibrous element are entangled with a sufficient number of the fibers of said fluid absorbent fibrous element to join said elements and said fluid-repellent element forms at least a portion of said body facing side.

34. The absorbent product of claim 33 wherein said effective amount of cationic repellent is an amount sufficient to cause said fibrous element to be not subject to wetting by fluids having a surface tension greater than about 45dynes/cm.

35. An absorbent product according to claim 33 wherein the step of joining said discrete fibrous material to said discrete absorbent material comprises vacuum-forming the materials.

36. An absorbent product having a body facing side and a garment facing side, having a discrete fluid absorbent fibrous element and a discrete fluid-repellent fibrous element, made by a process comprising the steps of:
 a) contacting a discrete fibrous pulp element with an effective repellent amount of one or more cationic repellents comprising a fatty acid ketene dimer, said effective repellent amount of cationic repellent comprising between about 0.19 and 0.34 weight % based on the total weight of said fibrous pulp element to form said discrete fluid-repellent fibrous element; and
 b) joining said discrete fluid-repellent fibrous element to said discrete absorbent fibrous element so as to form a unitized structure;
wherein a sufficient number of the fibers of said fluid-repellent fibrous element are entangled with a sufficient number of the fibers of said fluid absorbent fibrous element to join said elements and said discrete fluid-repellent fibrous element forms at least a portion of said body facing side.

37. A fluid-repellent fibrous material comprising a fibrous material sized with an effective repellent amount of one or more cationic repellents in a sizing treatment, the amount of said cationic repellent utilized in said sizing treatment being such that said fibrous material is not subject to wetting by fluids having a surface tension greater than about 45 dynes/cm.

38. The fluid-repellent fibrous material of claim 32 wherein said fibrous material is not subject to wetting by fluids having a surface tension greater than 40 dynes/cm.

39. The fluid-repellent fibrous material of claim 37 wherein said effective repellent amount of cationic repellent comprises at least about 0.19 weight % based on the total weight of the fibrous material.

40. The fluid-repellent fibrous material of claim 39 wherein said effective repellent amount of cationic repellent comprises between about 0.19 and 0.34 weight % based on the total weight of the fibrous material.

41. The fluid-repellent fibrous material of claim 39 wherein said fibrous material comprises pulp.

42. The fluid-repellent fibrous material of claim 37 wherein said cationic repellent comprises a fatty acid ketene dimer.

43. The fluid-repellent fibrous material of claim 37 wherein said fibrous material comprises pulp, said cationic repellent comprises a fatty acid ketene dimer, and said effective repellent amount of cationic repellent comprises between about 0.19 and 0.34 weight % based on the total weight Δ of the fibrous material pulp.

44. The fluid-repellent fibrous material of claim 37 which comprises a blend of fibrous material sized about 0.19 wt-% to about 0.34 wt-% of one or more cationic repellents and absorbent material, the blend of fibrous material not being subject to wetting by fluids having a surface tension greater than about 45 dynes/cm.

* * * * *